US010495643B2

(12) United States Patent
Glezer et al.

(10) Patent No.: US 10,495,643 B2
(45) Date of Patent: Dec. 3, 2019

(54) DIAGNOSTIC METHODS FOR LIVER DISORDERS

(71) Applicant: Meso Scale Technologies, LLC., Rockville, MD (US)

(72) Inventors: Eli N. Glezer, Del Mar, CA (US); Anu Mathew, North Potomac, MD (US); Martin Stengelin, Gaithersburg, MD (US); Mingyue Wang, Gaithersburg, MD (US)

(73) Assignee: MESO SCALE TECHNOLOGIES, LLC., Rockville, MD (US)

( * ) Notice: Subject to any disclaimer, the term of this patent is extended or adjusted under 35 U.S.C. 154(b) by 0 days.

(21) Appl. No.: 15/297,833

(22) Filed: Oct. 19, 2016

(65) Prior Publication Data

US 2017/0038388 A1    Feb. 9, 2017

Related U.S. Application Data

(63) Continuation of application No. 13/319,540, filed as application No. PCT/US2010/032886 on Apr. 29, 2010, now abandoned.

(60) Provisional application No. 61/216,081, filed on May 13, 2009.

(51) Int. Cl.
*G01N 33/574* (2006.01)

(52) U.S. Cl.
CPC ... *G01N 33/57438* (2013.01); *G01N 2333/47* (2013.01); *G01N 2333/4725* (2013.01); *G01N 2333/70503* (2013.01); *G01N 2400/00* (2013.01); *G01N 2800/085* (2013.01); *G01N 2800/56* (2013.01)

(58) Field of Classification Search
None
See application file for complete search history.

(56) References Cited

U.S. PATENT DOCUMENTS

| | | | |
|---|---|---|---|
| 4,168,146 A | 9/1979 | Grubb et al. | |
| 4,235,601 A | 11/1980 | Deutsch et al. | |
| 4,366,241 A | 12/1982 | Tom et al. | |
| 4,442,204 A | 4/1984 | Greenquist et al. | |
| 4,994,374 A | 2/1991 | Nishikawa et al. | |
| 5,208,535 A | 5/1993 | Nakayama et al. | |
| 5,807,522 A | 9/1998 | Brown et al. | |
| 6,110,426 A | 8/2000 | Shalon et al. | |
| 6,977,722 B2 | 12/2005 | Wohlstadter et al. | |
| 7,063,946 B2 | 6/2006 | Kenten et al. | |
| 7,497,997 B2 | 3/2009 | Glezer et al. | |
| 7,842,246 B2 | 11/2010 | Wohlstadter et al. | |
| 7,858,321 B2 | 12/2010 | Glezer et al. | |
| 7,981,362 B2 | 7/2011 | Glezer et al. | |
| 2003/0113713 A1 | 6/2003 | Glezer et al. | |
| 2003/0207290 A1 | 11/2003 | Kenten et al. | |
| 2004/0022677 A1 | 2/2004 | Wohlstadter et al. | |
| 2004/0147033 A1 | 7/2004 | Shriver et al. | |
| 2004/0189311 A1 | 9/2004 | Glezer et al. | |
| 2005/0052646 A1 | 3/2005 | Wohlstadter et al. | |
| 2005/0142033 A1 | 6/2005 | Glezer et al. | |
| 2006/0205012 A1 | 9/2006 | Debad et al. | |
| 2012/0058916 A1 | 3/2012 | Glezer et al. | |

FOREIGN PATENT DOCUMENTS

| | | |
|---|---|---|
| KR | 10-2003-0031243 | 4/2003 |
| WO | WO 99/26067 | 5/1999 |
| WO | WO 2004/058055 | 7/2004 |
| WO | WO 2007/056011 A2 | 5/2007 |

OTHER PUBLICATIONS

Attallah et al. (International Journal of Cancer Research 2(1): 50-56, 2006).*
Mathew et al. (Poster from Meso Scale Diagnostics, LLC, Rockville, Maryland, 2013).*
Ando E. et al., "Diagnostic Clues for Recurrent Hepatocellular Carcinoma: Comparison of Tumour Markers and Imaging Studies", Journal of Gastroenterology & Hepatology 15:641-648 (2003).
Berns A., "Gene Expression in Diagnosis", Cancer 403:491-492 (Feb. 3, 2000).
Chen et al., "Simultaneous Quantification of Six Human Cytokines in a Single Sample Using Microparticle-Based Flow Cytometric Technology", Clinical Chemistry 45(9):1693-1694 (1999).
Delehanty J.B., "Printing Functional Protein Microarrays Using Piezoelectric Capillaries", Methods in Molecular Biology 264:135-143 (2004).
Hanabata M. et al., "Immunohistochemical Study on Hepatic Tumors-KM01 Stains Compared with AFP, CEA, CA19-9 and RAS P21", Kobe J. Med. Sci. 37:81-96 (Apr. 1991).
Lovett R.A., "Toxicogenomics: Toxicologists Brace for Genomics Revolution", Science 289(5479):536-537 (Jul. 28, 2000).
Lue R.Y.P. et al., "Site-Specific Immobilization of Biotinylated Proteins for Protein Microarray Analysis", Methods in Molecular Biology 264:85-100 (2004).
Park M.K. et al., "A Latex Bead-Based Flow Cytometric Immunoassay Capable of Simultaneous Typing of Multiple Pnuemococcal Serotypes (Multibead Assay)", Clinical Diagnostic Laboratory Immunology 7(3):486-489 (May 2000).
Qin X-L et al., "Utility of Serum CA19-9 in Diagnosis of Cholangiocarcinoma: In Comparison With CEA", World J. Gastroenterol 10(3):427-432 (2004).
Sakamoto K. et al., "Comparative Effectiveness of the Tumour Diagnostics, CA 19-9, CA 125 and Carcinoembryonic Antigen in Patients With Diseases of the Digestive System", Gut 28:323-329 (1987).

(Continued)

*Primary Examiner* — Alana Harris Dent
(74) *Attorney, Agent, or Firm* — Scully, Scott, Murphy & Presser, P.C.

(57) ABSTRACT

The present invention relates to methods of diagnosing a liver disorder in a patient, as well as methods of monitoring the progression of a liver disorder and/or methods of monitoring a treatment protocol of a therapeutic agent or a chemotherapeutic regimen. The invention also relates to assay methods used in connection with the diagnostic methods described herein.

13 Claims, 10 Drawing Sheets

(56) References Cited

OTHER PUBLICATIONS

Skates S.J. et al., "Pooling of Case Specimens to Create Standard Serum Sets for Screening Cancer Biomarkers", Cancer Epidemiol Biomarkers Prev. 16(2):334-341 (2007).
Tannapfel A. et al., "Identification of Novel Proteins Associated With Hepatocellular Carcinomas Using Protein Microarrays", Journal of Pathology 201:238-249 (Aug. 2003).
Vignali D.A.A., "Multiplexed Particle-Based Flow Cytometric Assays", Journal of Immunological Methods 243:243-255 (2000).
Walt D.R., "Molecular Biology: Bead-Based Fiber-Optic Arrays", Science 287(5452):451-452 (Jan. 21, 2000).
Zhou L. et al., "Serum Tumor Markers for Detection of Hepatocellular Carcinoma", World J. Gastroenterology 12(8):1175-1181 (Feb. 2006).
International Search Report dated Jan. 14, 2011 received from the Korean Intellectual Property Office from International Application No. PCT/US2010/032886.

\* cited by examiner

DIAGNOSTIC METHODS FOR LIVER DISORDERS

CROSS-REFERENCE TO RELATED APPLICATIONS

The present application is a continuation application of U.S. patent application Ser. No. 13/319,540 filed on Nov. 9, 2011, which is a 371 of International application having Serial No. PCT/US2010/032886 filed on Apr. 29, 2010, which claims the benefit of U.S. Provisional Application No. 61/216,081 filed on May 13, 2009, the disclosures of which are incorporated herein by reference in their entirety.

FIELD OF THE INVENTION

This application relates to assay methods, modules and kits for conducting diagnostic assays useful in the detection and treatment of liver disorders.

BACKGROUND OF THE INVENTION

Challenges in the field of oncology include the lack of efficient means for early cancer detection and for specific cancer subtyping. There is a need for new cancer diagnostics that can provide early and specific diagnosis of cancer and enable targeted therapy and prognosis. The need for new diagnostics has been the impetus behind many initiatives targeting the discovery and development of new serum biomarkers for cancer. The hope is that the identification of suitable biomarkers will allow for the development of early cancer detection screening tests and will lead to improved cancer therapy and a reduction in the mortality associated with many cancers.

Alpha-Fetoprotein (AFP is included in the recommended list of biomarkers outlined by the National Academy of Clinical Biochemistry (NACB) in their Practice Guidelines and Recommendations For Use Of Tumor Markers In The Clinic, Liver Cancer (Section 3D) (Lamerz et al., National Academy of Clinical Biochemistry Guidelines for the Use of Tumor Markers in Primary Liver Cancer). The serum concentration of AFP in normal adults is, typically, less than 10 ng/mL. Serum AFP levels above 10 ng/mL may be indicative of cancer or chronic liver diseases, including hepatitis and liver cirrhosis. Levels greater than 400 to 500 ng/mL are considered indicative of human hepatocellular carcinoma (HCC) and may be used to discriminate HCC from chronic benign conditions, particularly if there is a sustained increase in AFP levels over time. However, not all hepatocellular carcinomas secrete AFP (e.g., the Fibrolamellar type do not). Still further, AFP could be elevated in pregnancy, in patients with other tumors of gonadal origin and in some patients with acute or chronic viral hepatitis without a tumor.

CA 125 is a serum biomarker associated primarily with epithelial ovarian cancer. While CA 125 levels are often elevated in liver cancer, it reportedly lacks specificity for HCC, as CA125 levels may also become elevated due to benign liver conditions, the presence of ascites or surgery (Bergmann et al. 1987; Collazos et al. 1992; Devarbhavi et al. 2002; Haglun et al. 1991; Kadayifci et al. 1996, 1997; Elias and Kew 1990; Miralles et al. 2003; Molina et al. 1991; Xiao and Liu, 2003).

CEA and CA 19-9 are serum biomarkers that are most commonly linked with colorectal cancer (CEA) and pancreatic and biliary tract cancer (CA 19-9). Previous studies have not found CEA or CA 19-9 to be significant biomarkers for liver cancer (Fabris et al. 1991; Leandro et al. 1989; Lopez et al. 1997; Maestranzi et al. 1998). There are studies suggesting use of CEA and CA 19-9 as tumor markers of the metastasis of colorectal cancer to the liver (Ishizuka et al. 2001; Lorenz et al. 1989).

Therefore, while the use of AFP as a biomarker for HCC has been documented, the value of CA 125, CEA and CA 19-9, alone or in combination with AFP, has not been recognized in the art. Moreover, the elevation of CEA, CA 19-9, OPN, MMP-9, E-cadherin, and erbB2 in patients with cirrhosis and/or HCC has not been observed to date.

SUMMARY OF THE INVENTION

The present invention provides a method for diagnosing HCC in a patient, wherein the method comprises (a) measuring a level of a first biomarker in a test sample obtained from a patient, wherein the first biomarker is selected from the group consisting of CEA, CA 125, CA 19-9; and (b) diagnosing from the measuring step the presence or absence of HCC in the patient.

The invention also provides a method for monitoring the progression of HCC in a patient diagnosed with HCC, wherein the method comprises (a) measuring the levels of a first biomarker in a plurality of samples obtained, at different times, from the patient, wherein the first biomarker is selected from the group consisting of CEA, CA 125, CA 19-9; and (b) determining from the levels of the first biomarker the progression or efficacy of treatment of the HCC.

The methods of the present invention may also include measuring a level of at least one additional biomarker in the sample and determining from the level of the first biomarker and the level of the at least one additional biomarker the presence or absence of HCC in the patient. Still further, the methods may further include comparing the level of the first biomarker in the sample to a level of the first biomarker in a normal control sample and diagnosing the presence or absence of HCC in the patient based on the comparison.

In addition, the methods may comprise comparing the level of the first biomarker and the at least one additional biomarker in the sample to levels of the first biomarker and the at least one additional biomarker in a normal control sample and diagnosing the presence or absence of HCC in the patient based on that comparison.

The at least one additional biomarker may be selected from the group consisting of AFP, OPN, MMP-9, E-cadherin, erbB2, and combinations thereof. Alternatively, the at least one additional biomarker may be selected from the group consisting of CEA, CA 125 and CA 19-9, provided that the additional biomarker is different from the first biomarker.

The diagnosing step of the instant methods may comprise comparing the level of the first biomarker to a detection cut-off level. Still further, the diagnosing step may comprise comparing the levels of the first biomarker and the at least one additional biomarker in the sample to detection cut-off levels for the biomarkers.

The methods may include determining from the level of the first biomarker the disease progression of HCC. And in one embodiment, the patient has been diagnosed with liver disease, e.g., cirrhosis, fibrosis, hepatitis, alcoholic liver disease, fatty liver disease, and combinations thereof. Moreover, the methods may also include subjecting the patient to an imaging method to evaluate the size, shape and position of the liver and the diagnosing step further comprises evaluating the presence or absence of HCC in the patient based on the results from the imaging method and the measuring step. In one embodiment, the imaging method is an ultrasound.

Still further, the present invention also provides a method for diagnosing cirrhosis in a patient suspected of having cirrhosis, wherein the method comprises (a) measuring a level of a first biomarker in a test sample obtained from a patient, wherein the first biomarker is selected from the group consisting of CEA, CA 125, CA 19-9; and (b) diagnosing from the measuring step the presence or absence of cirrhosis in the patient.

The invention also provides a method for monitoring the progression of cirrhosis in a patient diagnosed with cirrhosis, wherein the method includes (a) measuring the level(s) of a first biomarker in a plurality of samples obtained, at different times, from the patient, wherein the first biomarker is selected from the group consisting of CEA, CA 125, CA 19-9; and (1)) determining from the level(s) of the first biomarker the progression or efficacy of treatment of cirrhosis.

The methods of the invention may include measuring a level of at least one additional biomarker in the sample and determining from the level of the first biomarker and the level of the at least one additional biomarker the presence or absence of cirrhosis in said patient. Still further, the methods may also include comparing the level of the first biomarker in the sample to a level of the first biomarker in a normal control sample and diagnosing the presence or absence of cirrhosis in the patient based on the comparison. Moreover, in one embodiment, the methods further comprises comparing the level of the first biomarker and the at least one additional biomarker in the sample to levels of the first biomarker and the at least one additional biomarker in a normal control sample and diagnosing the presence or absence of cirrhosis in the patient based on the comparison. In these embodiments, the at least one additional biomarker may be selected from the group consisting of AFP, CEA, CA 125, CA 19-9, OPN, MMP-9, E-cadherin, erbB2, and combinations thereof. The methods may further comprise determining from the level of the first biomarker the disease progression of cirrhosis.

The levels of the first and the at least one additional biomarker measured in the methods of the present invention may be measured in a multiplexed assay. In one embodiment, the levels of the first and the at least one additional biomarker are measured in a single assay chamber. The assay chamber may be a single well of an assay plate or it may be a cartridge. In addition, the levels may be measured in an immunoassay.

The samples used in the methods of the invention may be blood, serum or plasma. Alternatively, the sample may be biopsy tissue, intestinal mucosa or urine.

DETAILED DESCRIPTION OF THE INVENTION

Figure 1A:
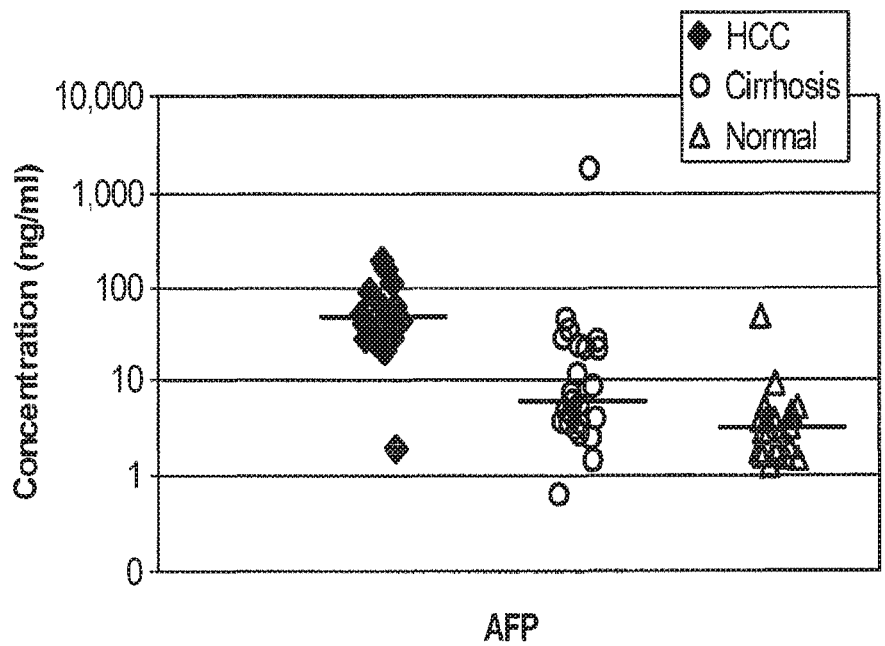
FIG. 1(A-H) shows the concentrations for various biomarkers in serum samples from HCC (♦), cirrhosis (○), and normal (Δ) patients, with median signal values indicated for each patient group. Each panel in FIG. 1 shows the calculated biomarker concentrations for AFP (Panel A), CA 19-9 (Panel B), CEA (Panel C), CA125 (Panel D), MMP-9 (Panel E), OPN (Panel F), E-cadherin (Panel G), and erbB2 (Panel H) in HCC (♦), cirrhosis (○), and normal (Δ) individual samples, with median signal values indicated for each sample group.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. The articles "a" and "an" are used herein to refer to one or to more than one (i.e., to at least one) of the grammatical object of the article. By way of example, "an element" means one element or more than one element.

The applicants have discovered that CEA, CA 125, and CA 19-9 are significantly elevated in sera of HCC patients, as compared to levels from cirrhotic or normal patients. The applicants have also discovered that CEA, CA 125 and CA 19-9 should be as efficient, if not superior, to AFP in diagnosing HCC and distinguishing HCC from cirrhosis. Furthermore, the applicants have discovered that combining the measurement of a marker from the group consisting of AFP, CEA, CA 125 and the measurement of at least one other marker from the same group and/or at least one marker selected from MMP-9, OPN, erbB2, and E-cadherin can detect HCC and/or cirrhosis in patients with a high degree of specificity.

Therefore, in one embodiment, the invention provides a method of diagnosing a cancerous condition in a patient by measuring, in a patient sample, a level of CEA, CA 125, CA 19-9, or combinations thereof and diagnosing the patient for the presence or absence of the cancerous condition. In another embodiment, at least two biomarkers selected from the group consisting of AFP, CEA, CA 125 and CA 19-9 are measured. The at least two markers can be measured in two independent assays conducted on one or more patient samples or the measurements can be conducted in a single multiplexed assay. Specific examples of this embodiment include the measurement, as independent or multiplexed measurements, of AFP and CEA, AFP and CA 125, AFP and CA 19-9 CEA and CA 125, CEA and CA 19-9 or CA 125 and CA 19-9. Additional examples include the independent or multiplexed measurements of AFP, CEA and CA 125; AFP, CA 125 and CA19-9 or CEA, CA 125 and CA 19-9.

The invention also includes a diagnostic method as described above, wherein one or more of AFP, CEA, CA 125 and CA 19-9 are measured, and the level of at least one additional biomarker is also measured (independently or in a multiplexed format) in the sample. Therefore, the levels of the first biomarker and the additional biomarker(s) in the test sample may be used to diagnose a cancerous condition in a patient. In one embodiment, the additional biomarker is selected from OPN, MMP-9, E-cadherin, erbB2, and combinations thereof. Other biomarkers or disease indices are known and may be measured/used in combination with the methods of the present invention, including and not limited to glypican 3, PIVKA II, ER6Q, Vimentin, actin alpha 1 skeletal muscle protein, hMFAP 4, tropomyosin, PTGES 2, amyloid P component, transgelin, calponin 1, *Homo sapiens* p20 protein, 17 kDa myosin light chain, H chain H Igg B12, prolyl 4-hydroxylase, beta subunit methylenetetrahydrofolate dehydrogenase 1, PR02619, aldehyde dehydrogenase 1, fibrinogen alpha chain preproprotein, fructose-bisphosphate aldolase B, argininosuccinate synthetase, Eefla2, AT P 5 A1, alpha-2 actin, regucalcin, serum albumin, mitochondrial malate dehydrogenase, mitochondrial acetoacetyl-CoA thiolase, Prothrombin, Gamma Glutamyl Transpeptidase, bilirubin, Apolipoprotein A1 (PGA) index, Age platelet (AP) index, Bonacini index, Pohl score, Foms index, Aspartate aminotransferase/Platelets Ratio index (APRI), MP3 (MMP1, PIINP) index, FIB4, Fibroindex and combinations thereof. In one embodiment, one or more cancer biomarkers (as described above) are measured in combination with one or more biomarkers of liver disease (for example, desgamma carboxyprothrombin (DCP), gamma-glutamyl-carboxylase, lectin-bound AFP, vitamin D binding protein (Go globulin), and/or liver fatty acid binding protein). In one example of such an embodiment, the combination of cancer markers and liver disease markers allows for better differentiation of liver cancer from non-cancerous liver diseases.

In one embodiment of the present invention, the level of the first biomarker and/or the level of the additional biomarkers in the test sample are compared to the levels of these biomarkers in a corresponding normal control sample. The difference between the normal control sample biomarker levels and that of the test sample may be the basis for diagnosing a cancerous condition in a patient. Alternatively, the level of the first biomarker is compared to a detection cut-off level or range, wherein the first biomarker level above or below the detection cut-off level (or within the detection cut-off range) is indicative of the cancerous condition. In addition, the diagnostic methods of the invention also contemplate comparing the level of the at least one additional biomarker to a detection cut-off level or range, wherein the at least one additional biomarker level above or below the detection cut-off level (or within a detection cut-off range) is indicative of the cancerous condition. Furthermore, the levels of the first and at least one additional marker may both be used to make a determination. For example, i) having a level of at least one of the markers above or below a detection cut-off level (or within a detection cut-off range) for that marker is indicative of the cancerous condition; ii) having the level of two or more (or all) of the markers above or below a detection cut-off level (or within a detection cut-off range) for each of the markers is indicative of the cancerous condition or iii) an algorithm based on the levels of the multiple markers is used to determine if the cancerous condition is present.

In addition, the methods of the present invention may be used in combination with other methods of diagnosing liver disease in a patient. Liver disease includes, e.g. cirrhosis, fibrosis, hepatitis, alcoholic liver disease, fatty liver disease, and combinations thereof. In one embodiment, the patient may also be subjected to one or more diagnostic tools designed to detect liver disease. For example, imaging methods may be used to provide images of the liver to look for tumors and blocked bile ducts and can be used to evaluate liver size and blood flow through the liver. In addition, a liver biopsy may be performed. Imaging methods that may be performed include abdominal ultrasound, computed tomography (CT) scan of the abdomen (including the liver, gallbladder, and spleen), magnetic resonance imaging (MRI) scan of the abdomen, and a liver and spleen scan. Still further, other tests that may be performed include, paracentesis, endoscopy, endoscopic retrograde cholangiopancreatogram, and ammonia testing.

The diagnostic methods of the present invention may be used to diagnose a variety of cancerous conditions, including hepatocellular carcinoma. As used herein, the term "cancer" is intended to mean a class of diseases characterized by the uncontrolled growth of aberrant cells, including all known cancers, and neoplastic conditions, whether characterized as malignant, benign, soft tissue or solid tumor. In one embodiment, the cancerous condition is malignant HCC. HCC is the fifth most common cancer worldwide and the third most common cause of cancer mortality, and is one of the few fastest increasing cancers in the U.S. Treatments for HCC improve survival only in those with early stage HCC. Despite improvements in survival rates for other cancers, the prognosis of HCC is still grim, with 1- and 3-year survival of 33% and 17%, respectively for patients diagnosed in 2002. The dismal prognosis is related to the insensitivities of the current diagnostic tools, alpha-fetoprotein (AFP) and liver ultrasound (US), which prevents detection of early stage HCC when treatment is most effective.

In addition, the diagnostic methods of the present invention may be used to identify cirrhosis. Cirrhosis is a term used to describe scarring of the liver and in advanced cirrhosis, excessive scar tissue inhibits proper liver function. Still further, the biomarkers identified herein may be used to diagnose hepatitis B virus (HBV) infection, hepatitis C virus (HCV) infections. Alternatively, the biomarkers may be used to diagnose fatty liver disease and/or alcoholic liver disease. Fatty liver disease can arise due to chronic alcohol ingestion. The causes of non-alcohol related fatty liver disease are not clearly defined, although risk factors include conditions such as obesity and type 2 diabetes Alcoholic liver disease is an acute form of alcohol-induced liver injury that occurs with the consumption of a large quantity of alcohol over a prolonged period of time. Liver disease may range in severity from asymptomatic derangement of biochemistries to fulminant liver failure and death.

The biomarkers identified by the applicants (i.e., AFP, CEA, CA 125, CA 19-9, OPN, MMP-9, E-cadherin, erbB2, alone or in combination with each other and/or in combination with other markers), may be used to diagnose one or more of these disorders in a patient, to assess the progression of one or more of these disorders in a patient, or to assess the efficacy of a treatment regimen for one or more of these disorders. In one embodiment of the invention, a patient that has been previously diagnosed with liver disease (e.g., cirrhosis, fibrosis, hepatitis, alcoholic liver disease, fatty liver disease, and combinations thereof), is evaluated for progression of that disorder to a cancerous condition. The level(s) of the various biomarkers identified herein may reflect the responsiveness or non-responsiveness of a hepatocellular carcinoma to a given treatment regimen. A response to a therapeutic regimen includes a detectable reduction to some extent of one or more of the symptoms of HCC, including, but not limited to: (1) reduction in the number of cancer cells; (2) reduction in tumor size; (3) inhibition (i.e., slowing to some extent, preferably stopping) of cancer cell infiltration into peripheral organs; (4) inhibition (i.e., slowing to some extent, preferably stopping) of tumor metastasis; (5) inhibition, to some extent, of tumor growth; (6) relieving or reducing to some extent one or more of the symptoms associated with the disorder; and/or (7) increasing, to some extent, the overall survival of a patient relative to that observed for the standard of care for HCC. A response to a therapeutic regimen may also comprise maintenance of a therapeutic benefit, including, but not limited to (1) inhibiting an increase in the number of cancer cells; (2) inhibiting an increase in tumor size; (3) inhibiting cancer cell infiltration into peripheral organs; (4) inhibiting tumor metastases; (5) relieving or reducing to some extent one or more of the symptoms associated with the disorder; and/or (6) inhibiting a recurrence or onset of one or more of the symptoms associated with the disorder.

In addition, the level of a biomarker may be determined at any time point before and/or after initiation of treatment. In one embodiment, the biomarker is used to gauge the efficacy of a therapeutic regimen. Therefore, the method of the present invention may include measuring a baseline level(s) of a biomarker before a therapeutic regimen is initiated, and the method may further comprise comparing the level and the baseline level. Moreover, the method may further comprise measuring an interim level of the biomarker during a therapeutic regimen and the method further comprises comparing the level, the interim level and the baseline level.

Alternatively, the measuring step may comprise measuring a level(s) of a biomarker before a therapeutic regimen is initiated to predict whether a HCC will be responsive or non-responsive to a given therapeutic regimen. The method may further comprise modifying the therapeutic regimen based on the level(s) of a biomarker observed during the measuring step, e.g., increasing or decreasing the dosage, frequency, or route of administration of a therapeutic agent, adding an additional therapeutic agent and/or palliative agent to a treatment regimen, or if the therapeutic regimen includes the administration of two or more therapeutic and/or palliative agents, the treatment regimen may be modified to eliminate one or more of the therapeutic and/or palliative agents used in the combination therapy.

As described herein, the measured levels of one or more biomarkers may be used to detect or monitor cancer (e.g., HCC) and/or to determine the responsiveness of a cancer to a specific treatment regimen. The specific methods/algorithms for using biomarker levels to make these determinations, as described herein, may optionally be implemented by software running on a computer that accepts the biomarker levels as input and returns a report with the determinations to the user. This software may run on a standalone computer or it may be integrated into the software/computing system of the analytical device used to measure the biomarker levels or, alternatively, into a laboratory information management system (LIMS) into which crude or processed analytical data is entered. In one embodiment, biomarkers are measured in a point-of-care clinical device which carries out the appropriate methods/algorithms for detecting, monitoring or determining the responsiveness of a cancer and which reports such determination(s) back to the user.

The assays of the present invention may be conducted by any suitable method. In one embodiment, the measuring step is conducted on a single sample, and it may be conducted in a single assay chamber or assay device, including but not limited to a single well of an assay plate, a single assay cartridge, a single lateral flow device, a single assay tube, etc.

As used herein, the term "sample" is intended to mean any biological fluid, cell, tissue, organ or combinations or portions thereof, which includes or potentially includes a biomarker of a disease of interest. For example, a sample can be a histologic section of a specimen obtained by biopsy, or cells that are placed in or adapted to tissue culture. A sample further can be a subcellular fraction or extract, or a crude or substantially pure nucleic acid molecule or protein preparation. In one embodiment, the samples that are analyzed in the assays of the present invention are blood or blood fractions such as, serum and plasma. Other suitable samples include biopsy tissue, intestinal mucosa and urine. In one embodiment, the level is measured using an immunoassay.

As used herein, a "biomarker" is a substance that is associated with a particular disease. A change in the levels of a biomarker may correlate with the risk or progression of a disease or with the susceptibility of the disease to a given treatment. A biomarker may be useful in the diagnosis of disease risk or the presence of disease in an individual, or to tailor treatments for the disease in an individual (choices of drug treatment or administration regimes). In evaluating potential drug therapies, a biomarker may be used as a surrogate for a natural endpoint such as survival or irreversible morbidity. If a treatment alters a biomarker that has a direct connection to improved health, the biomarker serves as a "surrogate endpoint" for evaluating clinical benefit A sample that is assayed in the diagnostic methods of the present invention may be obtained from any suitable patient, including but not limited to a patient suspected of having cancer, cirrhosis, HBV, HCV or alcoholic liver disease or a patient having a predisposition to one or more of these conditions. The patient may or may not exhibit symptoms associated with one or more of these conditions.

As used herein, the term "level" refers to the amount, concentration, or activity of a biomarker. The term "level" may also refer to the rate of change of the amount, concentration or activity of a biomarker. A level can be represented, for example, by the amount or synthesis rate of messenger RNA (mRNA) encoded by a gene, the amount or synthesis rate of polypeptide corresponding to a given amino acid sequence encoded by a gene, or the amount or synthesis rate of a biochemical form of a biomarker accumulated in a cell, including, for example, the amount of particular post-synthetic modifications of a biomarker such as a polypeptide, nucleic acid or small molecule. The term can be used to refer to an absolute amount of a biomarker in a sample or to a relative amount of the biomarker, including amount or concentration determined under steady-state or non-steady-state conditions. Level may also refer to an assay signal that correlates with the amount, concentration, activity or rate of change of a biomarker. The level of a biomarker can be determined relative to a control marker in a sample.

According to one aspect of the invention, the level(s) of biomarker(s) are measured in samples collected from individuals clinically diagnosed with, suspected of having or at risk of developing HCC. Initial diagnosis may have been carried out using conventional methods, e.g., biopsy or other conventional diagnostic methods. The level(s) of biomarker(s) are also measured in healthy individuals. Specific biomarkers valuable in distinguishing between normal and diseased patients are identified by visual inspection of the data, for example, by visual classification of data plotted on a one-dimensional or multidimensional graph, or by using statistical methods such as characterizing the statistically weighted difference between control individuals and diseased patients and/or by using Receiver Operating Characteristic (ROC) curve analysis. A variety of suitable methods for identifying useful biomarkers and setting detection thresholds/algorithms are known in the art and will be apparent to the skilled artisan.

For example and without limitation, diagnostically valuable biomarkers may be first identified using a statistically weighted difference between control individuals and diseased patients, calculated as $$\frac{D-N}{\sqrt{\sigma_D * \sigma_N}}$$

wherein D is the median level of a biomarker in patients diagnosed as having, for example, liver cancer, N is the median (or average) of the control individuals, $\sigma_D$ is the standard deviation of D and $\sigma_N$ is the standard deviation of N. The larger the magnitude, the greater the statistical difference between the diseased and normal populations.

According to one embodiment of the invention, biomarkers resulting in a statistically weighted difference between control individuals and diseased patients of greater than, e.g., 1, 1.5, 2, 2.5 or 3 could be identified as diagnostically valuable markers.

Another method of statistical analysis for identifying biomarkers is the use of z-scores, e.g., as described in Skates et al. (2007) Cancer Epidemiol. Biomarkers Prev. 16(2):334-341.

Another method of statistical analysis that can be useful in the inventive methods of the invention for determining the efficacy of particular candidate analytes, such as particular biomarkers, for acting as diagnostic marker(s) is ROC curve analysis. An ROC curve is a graphical approach to looking at the effect of a cut-off criterion, e.g., a cut-off value for a diagnostic indicator such as an assay signal or the level of an analyte in a sample, on the ability of a diagnostic to correctly identify positive or negative samples or subjects. One axis of the ROC curve is the true positive rate (TPR, i.e., the probability that a true positive sample/subject will be correctly identified as positive, or alternatively, the false negative rate (FNR=1−TPR, the probability that a true positive sample/subject will be incorrectly identified as a negative). The other axis is the true negative rate, i.e., TNR, the probability that a true negative sample will be correctly identified as a negative, or alternatively, the false positive rate (FPR=1−TNR, the probability that a true negative sample will be incorrectly identified as positive). The ROC curve is generated using assay results for a population of samples/subjects by varying the diagnostic cut-off value used to identify samples/subjects as positive or negative and plotting calculated values of TPR or FNR and TNR or FPR for each cut-off value. The area under the ROC curve (referred to herein as the AUC) is one indication of the ability of the diagnostic to separate positive and negative samples/subjects. In one embodiment, a biomarker provides an AUC≥0.7. In another embodiment, a biomarker provides an AUC≥0.8. In another embodiment, a biomarker provides an AUC≥0.9.

Diagnostic indicators analyzed by ROC curve analysis may be a level of an analyte, e.g., a biomarker, or an assay signal. Alternatively, the diagnostic indicator may be a function of multiple measured values, for example, a function of the level/assay signal of a plurality of analytes, e.g., a plurality of biomarkers, or a function that combines the level or assay signal of one or more analytes with a patient's scoring value that is determined based on visual, radiological and/or histological evaluation of a patient. The multi-parameter analysis may provide more accurate diagnosis relative to analysis of a single marker.

Candidates for a multi-analyte panel could be selected by using criteria such as individual analyte ROC areas, median difference between groups normalized by geometric inter-quartile range (IQR) etc. The objective is to partition the analyte space to improve separation between groups (for example, normal and disease populations) or to minimize the misclassification rate.

One approach is to define a panel response as a weighted combination of individual analytes and then compute an objective function like ROC area, product of sensitivity and specificity, etc., See e.g., WO 2004/058055, as well as US2006/0205012, the disclosures of which are incorporated herein by reference in their entireties.

Biomarker levels may be measured using any of a number of techniques available to the person of ordinary skill in the art, e.g., direct physical measurements (e.g., mass spectrometry) or binding assays (e.g., immunoassays, agglutination assays and immunochromatographic assays). The method may also comprise measuring a signal that results from a chemical reactions, e.g., a change in optical absorbance, a change in fluorescence, the generation of chemiluminescence or electrochemiluminescence, a change in reflectivity, refractive index or light scattering, the accumulation or release of detectable labels from the surface, the oxidation or reduction or redox species, an electrical current or potential, changes in magnetic fields, etc. Suitable detection techniques may detect binding events by measuring the participation of labeled binding reagents through the measurement of the labels via their photoluminescence (e.g., via measurement of fluorescence, time-resolved fluorescence, evanescent wave fluorescence, up-converting phosphors, multi-photon fluorescence, etc.), chemiluminescence, electrochemiluminescence, light scattering, optical absorbance, radioactivity, magnetic fields, enzymatic activity (e.g., by measuring enzyme activity through enzymatic reactions that cause changes in optical absorbance or fluorescence or cause the emission of chemiluminescence). Alternatively, detection techniques may be used that do not require the use of labels, e.g., techniques based on measuring mass (e.g., surface acoustic wave measurements), refractive index (e.g., surface plasmon resonance measurements), or the inherent luminescence of an analyte.

Binding assays for measuring biomarker levels may use solid phase or homogenous formats. Suitable assay methods include sandwich or competitive binding assays. Examples of sandwich immunoassays are described in U.S. Pat. Nos. 4,168,146 and 4,366,241, both of which are incorporated herein by reference in their entireties. Examples of competitive immunoassays include those disclosed in U.S. Pat. Nos. 4,235,601, 4,442,204 and 5,208,535, each of which are incorporated herein by reference in their entireties.

Multiple biomarkers may be measured using a multiplexed assay format, e.g., multiplexing through the use of binding reagent arrays, multiplexing using spectral discrimination of labels, multiplexing of flow cytometric analysis of binding assays carried out on particles, e.g., using the Luminex® system. Suitable multiplexing methods include array based binding assays using patterned arrays of immobilized antibodies directed against the biomarkers of interest. Various approaches for conducting multiplexed assays have been described (See e.g., US 20040022677; US 20050052646; US 20030207290; US 20030113713; US 20050142033; and US 20040189311, each of which is incorporated herein by reference in their entireties. One approach to multiplexing binding assays involves the use of patterned arrays of binding reagents, e.g., U.S. Pat. Nos. 5,807,522 and 6,110,426; Delehanty J-B., Printing functional protein microarrays using piezoelectric capillaries, Methods Mol. Bio. (2004) 278: 135-44; Lue R Y et. al., Site-specific immobilization of biotinylated proteins for protein microarray analysis, Methods Mol. Biol. (2004) 278: 85-100; Lovett, Toxicogenomics: Toxicologists Brace for Genomics Revolution, Science (2000) 289: 536-537; Berns A, Cancer: Gene expression in diagnosis, nature (2000), 403,491-92; Walt, Molecular Biology: Bead-based Fiber-Optic Arrays, Science (2000) 287: 451-52 for more details). Another approach involves the use of binding reagents coated on beads that can be individually identified and interrogated. See e.g., WO 9926067, which describes the use of magnetic particles that vary in size to assay multiple analytes; particles belonging to different distinct size ranges are used to assay different analytes. The particles are designed to be distinguished and individually interrogated by flow cytometry. Vignali has described a multiplex binding assay in which 64 different bead sets of microparticles are employed, each having a uniform and distinct proportion of two dyes (Vignali, D. A A, "Multiplexed Particle-Based Flow Cytometric Assays" J. ImmunoL Meth. (2000) 243: 243-55). A similar approach involving a set of 15 different beads of differing size and fluorescence has been disclosed as useful for simultaneous typing of multiple pneumococcal serotypes (Park, M. K. et at, "A Latex Bead-Based Flow Cytometric Immunoassay Capable of Simultaneous Typing of Multiple Pneumococcal Serotypes (Multibead Assay)" Clin. Diag. Lab ImmunoL (2000) 7: 4869), Bishop, J E et al. have described a multiplex sandwich assay for simultaneous quantification of six human cytokines (Bishop. L E. et al., "Simultaneous Quantification of Six Human Cytokines in a Single Sample Using Microparticle-based Flow Cytometric Technology," Clin. Chem (1999) 45:1693-1694).

A diagnostic test may be conducted in a single assay chamber, such as a single well of an assay plate or an assay chamber that is an assay chamber of a cartridge. The assay modules, e.g., assay plates or cartridges or multi-well assay plates), methods and apparatuses for conducting assay measurements suitable for the present invention are described for example, in US 20040022677; US 20050052646; US 20050142033; US 20040189311, each of which is incorporated herein by reference in their entireties. Assay plates and plate readers are now commercially available (MULTI-SPOT® and MULTI-ARRAY® plates and SECTOR® instruments, Meso Scale Discovery®, a division of Meso Scale Diagnostics, LLC, Gaithersburg, Md.).

The following non-limiting examples serve to illustrate rather than limit the present invention.

EXAMPLES

Example 1

Measurement of 10 Potential Biomarkers in Serum of HCC, Cirrhotic, and Normal Patients In order to identify biomarkers useful for diagnosis of HCC, 25 serum samples from patients with primary HCC (Table 1), 25 samples from patients with alcohol-induced or fatty liver disease-induced cirrhosis (Table 2), and 30 samples (serum) from apparently normal individuals were obtained and screened for ten potential biomarkers (AFP, CEA, CA 125, CA 19-9, OPN, MMP-9, E-cadherin, erbB2, EGFR, and cKit) using a multiplexed immunoassay format.

TABLE 1

HCC patient samples with associated treatment and HCC stage information, obtained from Bioreclamation, Inc. (5FU refers to 5-Fluorouracil).

| GENDER | AGE (years) | MEDICATIONS | STAGE |
|---|---|---|---|
| FEMALE | 46 | None | 2 |
| FEMALE | 49 | 5FU | 2 |
| FEMALE | 47 | Zometa | 3 |
| FEMALE | 52 | None | 2 |
| FEMALE | 50 | 5FU | 3 |
| MALE | 57 | None | 2 |
| FEMALE | 47 | 5FU | 3 |
| FEMALE | 78 | Zometa | 3 |
| FEMALE | 74 | Avastin, 5FU | 2 |
| FEMALE | 66 | Gemzar | 4 |
| MALE | 58 | None | 2 |
| MALE | 63 | Zometa | 2 |
| FEMALE | 38 | None | 2 |
| FEMALE | 48 | 5FU | 3 |
| MALE | 57 | Gemzar | 2 |
| MALE | 71 | Carboplatin | 2 |
| FEMALE | 74 | Zometa, 5FU | 3 |
| FEMALE | 62 | Avastin, Carboplatin | 2 |
| FEMALE | 77 | None | 2 |
| MALE | 63 | Avastin, 5FU | 2 |
| FEMALE | 65 | 5FU | 3 |
| MALE | 67 | Zometa | 2 |
| FEMALE | 58 | Gemzar | 2 |
| FEMALE | 62 | None | 2 |
| FEMALE | 61 | Carboplatin | 2 |
| | Average age | 60 | |
| | Median age | 61 | |

TABLE 2

Cirrhosis samples obtained from Bioreclamation, Inc

| CIRRHOSIS TYPE | GENDER | AGE (years) |
|---|---|---|
| ALCOHOL INDUCED | Male | 54 |
| ALCOHOL INDUCED | Male | 52 |
| ALCOHOL INDUCED | Female | 41 |
| ALCOHOL INDUCED | Male | 43 |
| ALCOHOL INDUCED | Male | 49 |
| ALCOHOL INDUCED | Male | 50 |
| ALCOHOL INDUCED | Male | 57 |
| ALCOHOL INDUCED | Female | 49 |
| ALCOHOL INDUCED | Female | 53 |
| ALCOHOL INDUCED | Male | 45 |
| ALCOHOL INDUCED | Male | 53 |
| ALCOHOL INDUCED | Female | 61 |
| ALCOHOL INDUCED | Male | 55 |
| FATTY LIVER DISEASE INDUCED | Female | 83 |
| FATTY LIVER DISEASE INDUCED | Female | 50 |
| FATTY LIVER DISEASE INDUCED | Male | 56 |
| FATTY LIVER DISEASE INDUCED | Male | 52 |
| FATTY LIVER DISEASE INDUCED | Male | 60 |
| FATTY LIVER DISEASE INDUCED | Male | 59 |
| FATTY LIVER DISEASE INDUCED | Male | 56 |
| FATTY LIVER DISEASE INDUCED | Male | 72 |
| FATTY LIVER DISEASE INDUCED | Male | 48 |
| FATTY LIVER DISEASE INDUCED | Female | 69 |
| FATTY LIVER DISEASE INDUCED | Male | 65 |
| FATTY LIVER DISEASE INDUCED | Male | 58 |
| | Average age | 56 |
| | Median age | 54 |

Each sample in Tables 1 and 2 as well as the normal serum samples were analyzed using a Multi-Spot® 96-well 10-plex Cancer Plate (Meso Scale Discovery, LLC, Gaithersburg, Md.). Each well of these plates has a 10-plex array of capture antibodies against the 10 target biomarkers (AFP, CEA, CA 125, CA 19-9, OPN, MMP-9, E-cadherin, erbB2, EGFR, and cKit). The antibody arrays are printed on integrated carbon ink electrodes to allow for electrochemiluminescence-based detection.

Figure 1B:
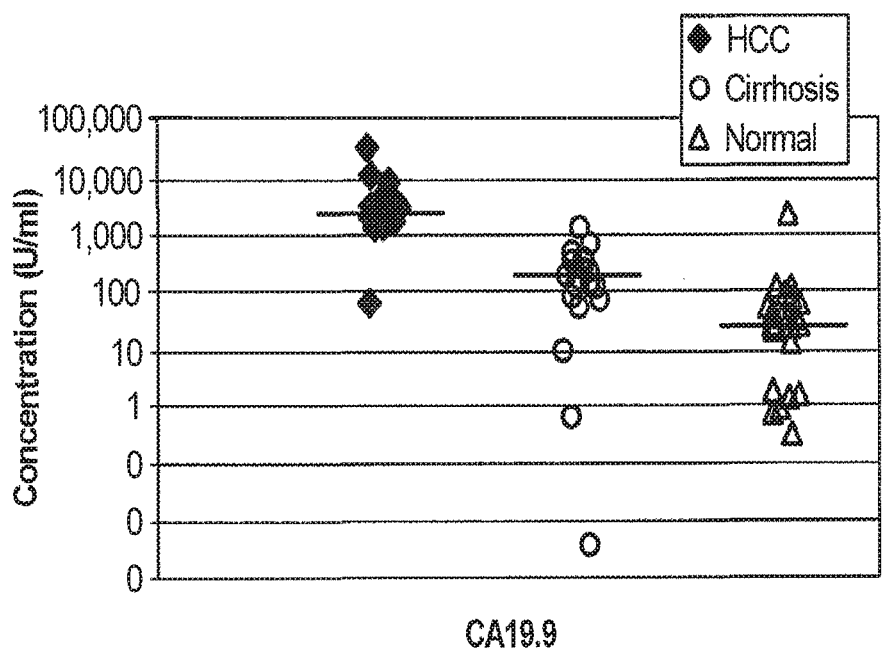
Figure 1C:
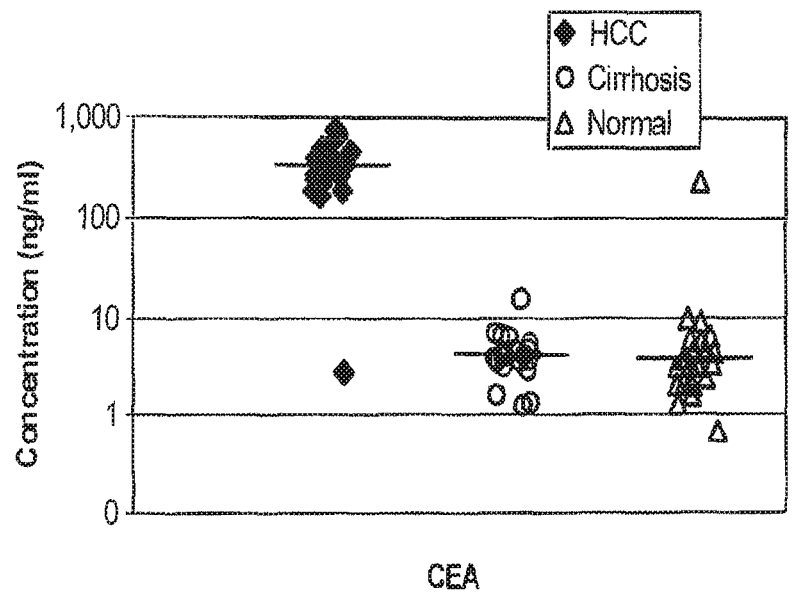
Figure 1D:
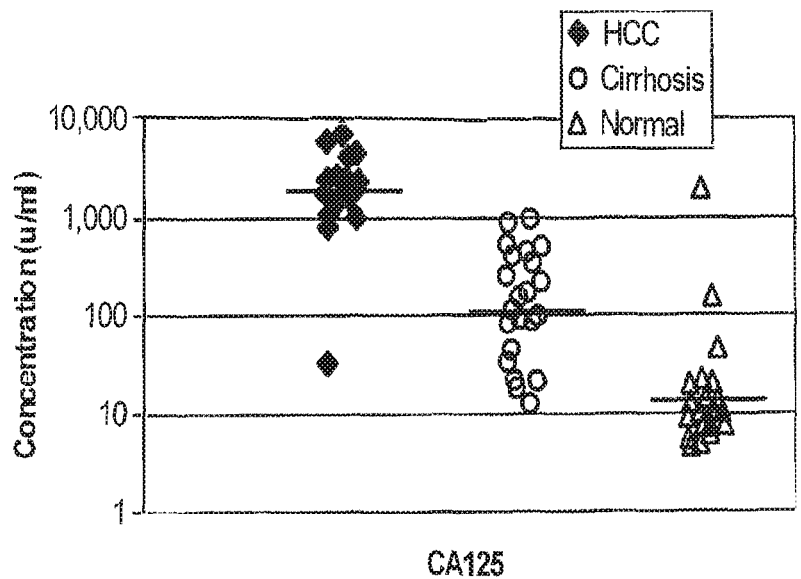
Figure 1E:
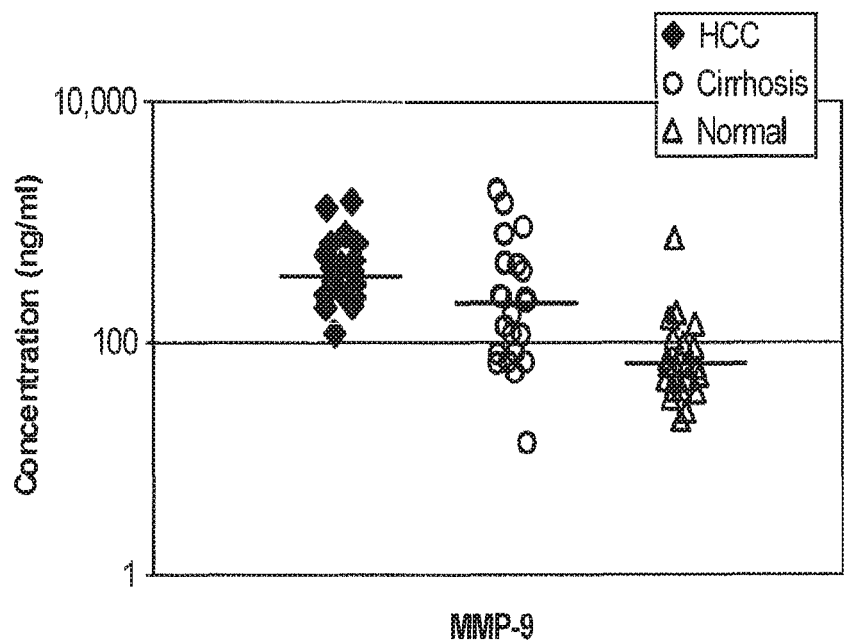
Figure 1F:
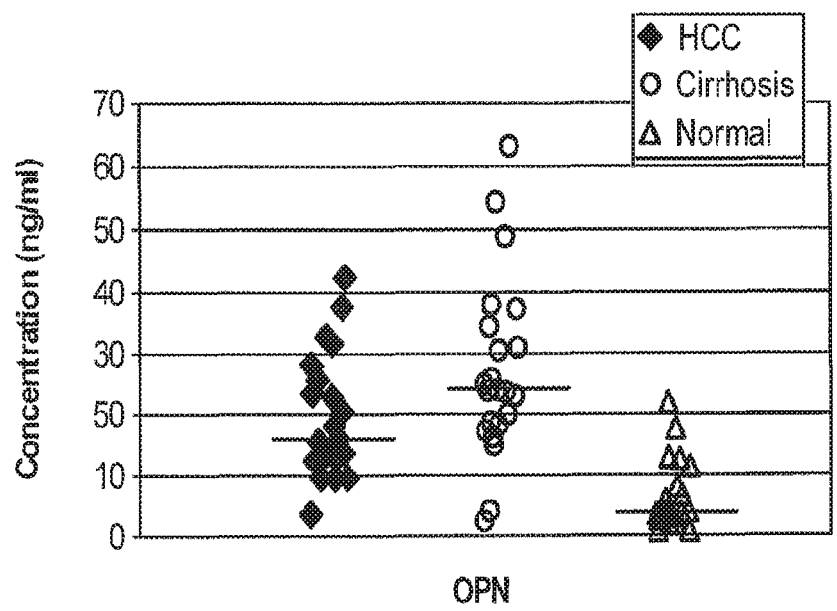
Figure 1G:
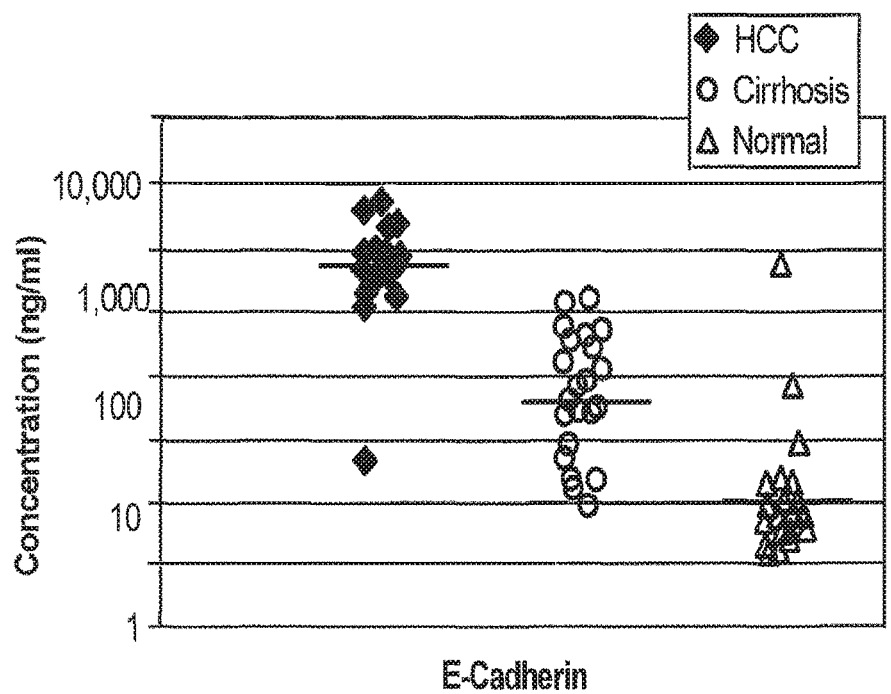
Figure 1H:
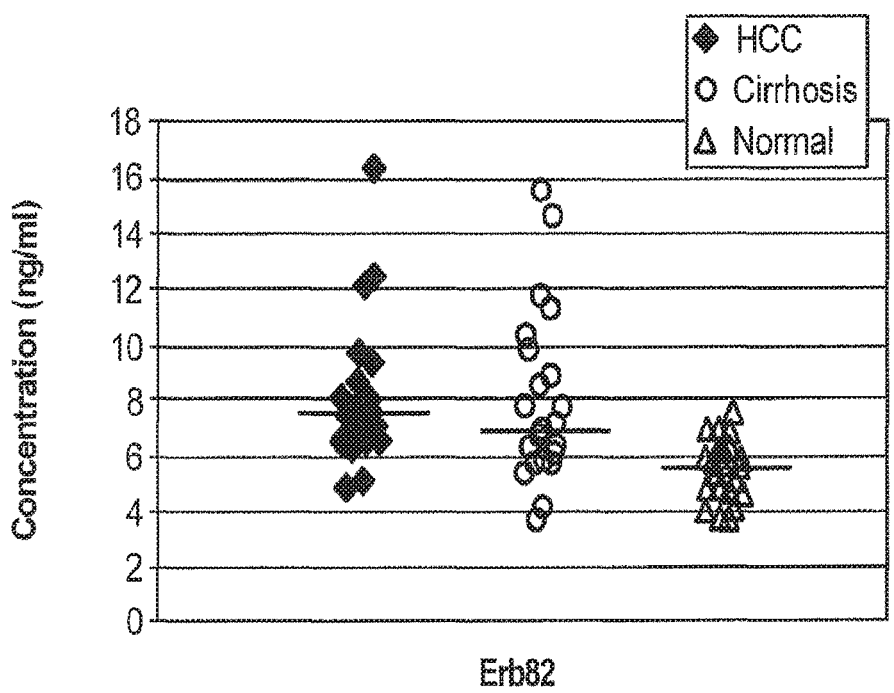

The samples were analyzed using the following assay protocol: The 10-plex Cancer Plate (also supplied by Meso Scale Discovery, LLC), was blocked for 1 hour using a suitable blocking solution (MSD Blocker A, also supplied by Meso Scale Discovery, LLC), and subsequently washed using a washing buffer (PBS/Tween). Twenty five uL of an assay diluent was added to each well, followed by 25 uL of a five-fold dilution of the sample (diluted in the assay diluent), The plate was incubated with shaking for about 2 hours, and washed. Twenty five uL of a mixture containing labeled detection antibodies against the 10 targets was added to each well and the plate was incubated with shaking for 2 hour. The labels used were electrochemiluminescent Sulfo-TAG™ labels (Meso Scale Discovery, LLC). The plate was washed, 150 uL of Read Buffer T (Meso Scale Discovery, LLC) was added and the plates were read using a Sector Imager 6000 electrochemiluminescence plate reader (Meso Scale Discovery, LLC). The reader reports assay signals for each array element in relative ECL units. Concentrations (Table 3) were calculated from the ECL values based on calibration curves generated with protein standards. The average and individual concentrations of each analyte for each sample type are plotted in FIG. 1.

TABLE 3

Measured concentrations of AFP, CEA, CA 125, CA 19-9, OPN, MMP-9, E-cadherin, erbB2, EGFR and cKit in the HCC, cirrhosis, and normal serum samples described above.

| | Sample ID | AFP (ng/ml) | CA 19-9 (U/ml) | CA 125 (U/ml) | CEA (ng/ml) | cKit (ng/ml) | E-Cadherin (ng/ml) | ErbB2 (ng/ml) | MMP-9 (ng/ml) | OPN (ng/ml) | EGFR (ng/ml) |
|---|---|---|---|---|---|---|---|---|---|---|---|
| Liver Cancer Samples | BRH223908 | 103 | 7,188 | 4,368 | 471 | 105 | 28 | 13 | 341 | 38 | 117 |
| | BRH223909 | 49 | 3,090 | 2,100 | 360 | 124 | 32 | 9 | 415 | 23 | 102 |
| | BRH223910 | 185 | 28,853 | 7,035 | 675 | 98 | 53 | 16 | 200 | 42 | 117 |
| | BRH223911 | 64 | 3,837 | 2,295 | 415 | 118 | 32 | 7 | 615 | 26 | 102 |
| | BRH223912 | 88 | 8,478 | 4,078 | 469 | 123 | 29 | 10 | 214 | 32 | 113 |
| | BRH223913 | 61 | 3,953 | 2,497 | 342 | 111 | 32 | 9 | 267 | 28 | 107 |
| | BRH223914 | 143 | 11,112 | 6,008 | 722 | 106 | 41 | 12 | 193 | 32 | 119 |
| | BRH223915 | 44 | 3,703 | 1,712 | 267 | 119 | 29 | 8 | 475 | 14 | 120 |
| | BRH223916 | 26 | 1,547 | 1,074 | 165 | 115 | 22 | 7 | 418 | 16 | 146 |
| | BRH223917 | 52 | 2,494 | 2,085 | 322 | 98 | 33 | 7 | 764 | 23 | 110 |
| | BRH223918 | 38 | 2,006 | 1,480 | 257 | 128 | 46 | 9 | 474 | 12 | 155 |
| | BRH223919 | 42 | 2,168 | 1,695 | 246 | 137 | 39 | 7 | 1,321 | 20 | 126 |
| | BRH223920 | 50 | 2,366 | 2,165 | 288 | 143 | 32 | 7 | 533 | 16 | 123 |
| | BRH223921 | 29 | 1,746 | 1,247 | 221 | 125 | 47 | 8 | 617 | 10 | 128 |
| | BRH223922 | 43 | 2,422 | 1,731 | 306 | 113 | 37 | 8 | 460 | 16 | 120 |
| | BRH223923 | 29 | 1,756 | 1,040 | 187 | 136 | 78 | 8 | 290 | 25 | 108 |
| | BRH223924 | 22 | 1,392 | 830 | 182 | 84 | 18 | 6 | 652 | 10 | 127 |
| | BRH223925 | 26 | 1,489 | 939 | 236 | 89 | 36 | 5 | 299 | 10 | 113 |
| | BRH223926 | 63 | 3,479 | 2,335 | 451 | 90 | 43 | 8 | 312 | 13 | 100 |
| | BRH223927 | 48 | 2,482 | 1,893 | 440 | 129 | 51 | 7 | 234 | 14 | 135 |
| | BRH223928 | 44 | 2,302 | 1,830 | 368 | 112 | 28 | 7 | 291 | 12 | 97 |
| | BRH223929 | 54 | 3,032 | 2,304 | 308 | 93 | 29 | 8 | 242 | 15 | 115 |
| | BRH223930 | 64 | 3,421 | 2,576 | 439 | 100 | 43 | 8 | 256 | 13 | 127 |
| | BRH223931 | 40 | 2,832 | 1,565 | 386 | 93 | 20 | 7 | 1,527 | 18 | 98 |
| | BRH223932 | 2 | 65 | 32 | 3 | 154 | 14 | 5 | 116 | 4 | 130 |
| Cirrhosis Samples | BRH241658 | 4 | 146 | 215 | 5 | 87 | 24 | 16 | 222 | 38 | 104 |
| | BRH241659 | 3 | 168 | 956 | 5 | 101 | 29 | 7 | 66 | 30 | 97 |
| | BRH241660 | 1 | 609 | 34 | 1 | 213 | 16 | 6 | 929 | 3 | 91 |
| | BRH241661 | 21 | 334 | 530 | 4 | 106 | 55 | 7 | 76 | 24 | 80 |
| | BRH241662 | 26 | 363 | 245 | 4 | 112 | 76 | 7 | 135 | 37 | 68 |
| | BRH241663 | 6 | 207 | 21 | 6 | 95 | 34 | 12 | 799 | 4 | 112 |
| | BRH241664 | 6 | 194 | 485 | 6 | 102 | 37 | 10 | 437 | 25 | 121 |
| | BRH241665 | 3 | 312 | 89 | 2 | 131 | 10 | 6 | 199 | 15 | 93 |
| | BRH241666 | 8 | 51 | 46 | 3 | 103 | 67 | 11 | 63 | 23 | 165 |
| | BRH241667 | 1 | 1 | 16 | 5 | 111 | 143 | 4 | 1,838 | 63 | 143 |
| | BRH241668 | 2 | 131 | 399 | 4 | 93 | 100 | 5 | 1,466 | 49 | 115 |
| | BRH241669 | 4 | 1,259 | 332 | 15 | 118 | 132 | 8 | 54 | 26 | 111 |
| | BRH241670 | 5 | 171 | 922 | 7 | 101 | 59 | 15 | 110 | 35 | 106 |
| | BRH241671 | 3 | 209 | 81 | 1 | 162 | 135 | 9 | 13 | 54 | 75 |
| | BRH241672 | 12 | 468 | 94 | 4 | 174 | 34 | 10 | 215 | 31 | 127 |
| | BRH241673 | 1.767 | 80 | 448 | 4 | 137 | 48 | 6 | 121 | 24 | 108 |
| | BRH241674 | 23 | 309 | 113 | 3 | 125 | 47 | 9 | 225 | 18 | 141 |
| | BRH241675 | 37 | 391 | 178 | 6 | 146 | 79 | 8 | 216 | 20 | 117 |
| | BRH241676 | 24 | 319 | 92 | 4 | 124 | 64 | 6 | 235 | 19 | 111 |
| | BRH241677 | 44 | 419 | 149 | 5 | 132 | 82 | 7 | 168 | 23 | 79 |
| | BRH241678 | 27 | 406 | 166 | 4 | 106 | 63 | 7 | 217 | 24 | 94 |
| | BRH241679 | 5 | 87 | 78 | 4 | 38 | 55 | 4 | 457 | 18 | 111 |
| | BRH241680 | 5 | 11 | 21 | 4 | 93 | 40 | 6 | 375 | 15 | 109 |
| | BRH241681 | 21 | 298 | 108 | 4 | 154 | 43 | 8 | 311 | 16 | 121 |
| | BRH241682 | 9 | 0.00 | 11 | 6 | 195 | 51 | 6 | 61 | 24 | 132 |
| Normal Samples | BRH202043 | 3 | 73 | 11 | 7 | 92 | 27 | 6 | 35 | 5 | 98 |
| | BRH202044 | 2 | 47 | 6 | 8 | 160 | 42 | 4 | 65 | 2 | 105 |
| | BRH202045 | 3 | 0 | 9 | 3 | 122 | 23 | 5 | 141 | 1 | 104 |
| | BRH202046 | 2 | 25 | 6 | 9 | 188 | 29 | 5 | 67 | 1 | 106 |
| | BRH202047 | 5 | 29 | 6 | 10 | 120 | 18 | 4 | 121 | 1 | 116 |
| | BRH202048 | 2 | 15 | 46 | 3 | 116 | 29 | 5 | 77 | 4 | 88 |
| | BRH202049 | 2 | 30 | 8 | 2 | 136 | 11 | 4 | 74 | 3 | 99 |

TABLE 3-continued

Measured concentrations of AFP, CEA, CA 125, CA 19-9, OPN, MMP-9, E-cadherin, erbB2, EGFR and cKit in the HCC, cirrhosis, and normal serum samples described above.

| Sample ID | AFP (ng/ml) | CA 19-9 (U/ml) | CA 125 (U/ml) | CEA (ng/ml) | cKit (ng/ml) | E-Cadherin (ng/ml) | ErbB2 (ng/ml) | MMP-9 (ng/ml) | OPN (ng/ml) | EGFR (ng/ml) |
|---|---|---|---|---|---|---|---|---|---|---|
| BRH202050 | 2 | 2 | 8 | 2 | 110 | 16 | 4 | 38 | 13 | 118 |
| BRH202051 | 4 | 46 | 13 | 4 | 112 | 25 | 8 | 50 | 4 | 122 |
| BRH202052 | 2 | 30 | 19 | 2 | 147 | 18 | 7 | 64 | 2 | 138 |
| BRH202053 | 5 | 30 | 12 | 4 | 143 | 28 | 7 | 50 | 8 | 125 |
| BRH202054 | 4 | 63 | 18 | 4 | 203 | 16 | 4 | 49 | 3 | 127 |
| BRH202055 | 2 | 83 | 22 | 1 | 158 | 27 | 7 | 61 | 2 | 128 |
| BRH202056 | 2 | 100 | 6 | 5 | 254 | 21 | 6 | 54 | 6 | 128 |
| BRH202057 | 2 | 1 | 13 | 2 | 184 | 22 | 5 | 60 | 12 | 129 |
| BRH202058 | 3 | 2 | 18 | 1 | 76 | 16 | 6 | 22 | 4 | 143 |
| BRH202059 | 4 | 88 | 14 | 4 | 71 | 10 | 5 | 53 | 2 | 166 |
| BRH202060 | 3 | 32 | 14 | 3 | 156 | 30 | 5 | 38 | 3 | 150 |
| BRH202061 | 9 | 99 | 157 | 2 | 140 | 33 | 6 | 68 | 3 | 166 |
| BRH202062 | 4 | 138 | 23 | 5 | 159 | 31 | 4 | 67 | 2 | 141 |
| BRH177512 | 3 | 0 | 11 | 3 | 249 | 27 | 6 | 82 | 8 | 127 |
| BRH177513 | 5 | 0 | 6 | 4 | 159 | 26 | 7 | 179 | 4 | 147 |
| BRH177514 | 1 | 62 | 19 | 3 | 137 | 22 | 5 | 64 | 4 | 118 |
| BRH177515 | 1 | 27 | 6 | 3 | 120 | 25 | 6 | 26 | 21 | 155 |
| BRH177516 | 4 | 37 | 18 | 2 | 171 | 20 | 7 | 40 | 4 | 140 |
| BRH177517 | 2 | 65 | 5 | 7 | 95 | 16 | 5 | 75 | 5 | 105 |
| BRH177518 | 5 | 1 | 5 | 4 | 122 | 57 | 7 | 85 | 6 | 144 |
| BRH177519 | 3 | 2 | 17 | 7 | 231 | 57 | 7 | 87 | 18 | 219 |
| BRH177520 | 48 | 2,348 | 2,053 | 241 | 70 | 24 | 6 | 158 | 13 | 67 |
| BRH177523 | 4 | 125 | 19 | 5 | 97 | 46 | 6 | 706 | 7 | 181 |

Example 2

Identification of Biomarkers for Distinguishing Normal, HCC and/or Cirrhotic Patients The ability of the individual markers AFP, CEA, CA 125, CA 19-9, OPN, MMP-9, E-cadherin, and erbB2 to detect primary HCC and/or cirrhosis is summarized in Table 4 as calculated AUC (area under the curve) values from ROC (Receiver Operating Characteristic) curves. The levels of AFP, CEA, CA 125, and CA 19-9 were found to be significantly elevated in the HCC samples, as compared to levels in the cirrhosis and normal samples. The performance of the CA 125, CA 19-9, and CEA assays were comparable, if not superior, to performance of AFP in distinguishing HCC samples from normal samples, HCC samples from cirrhosis samples, and/or cirrhosis samples from normal samples. The levels of OPN, MMP-9, E-cadherin, and ErbB2 were also significantly altered in the different sample types and also showed utility in distinguishing HCC and cirrhosis samples from normals.

TABLE 4

Area under curve (AUC) values calculated from ROC curves generated using the data generated for the MSD Cancer 10-plex assay panel and the HCC, cirrhosis and normal serum samples (see Example 1). AUC values are provided for ROC analysis of each biomarker's ability to distinguish HCC samples from normal samples (HCC/normal), HCC samples from cirrhosis samples (HCC/cirrhosis), and cirrhosis samples from normal sample (cirrhosis).

| | AUC values from ROC curves | | | | | | | |
|---|---|---|---|---|---|---|---|---|
| | E-cad | erbB2 | AFP | CA 125 | CA 19-9 | CEA | MMP-9 | OPN |
| HCC/normal | 0.72 | 0.85 | 0.92 | 0.88 | 0.95 | 0.93 | 0.93 | 0.89 |
| HCC/cirrhosis | 0.16 | 0.54 | 0.85 | 0.92 | 0.93 | 0.92 | 0.67 | 0.28 |
| cirrhosis/normal | 0.86 | 0.78 | 0.76 | 0.87 | 0.81 | 0.54 | 0.82 | 0.91 |

The data for the top four markers, AFP, CA 19-9, CA 125 and CEA, were also used to derive scores of normalized median differences between the three classes of samples, as another means of determining the specificity of the markers in distinguishing the disease states from normals and from each other (Table 5). Scores with a magnitude ≥1 indicate that the biomarker has utility in distinguishing between two classes of samples with increasing scores (e.g., scores with magnitudes ≥2 or ≥3) indicating increasing discriminating ability. According to this analysis approach, CA 19.9 performs almost as well as AFP in both discriminating HCC from cirrhosis and from normals, and CA 125 and CEA perform better than AFP in both categories. CEA had scores >3 for distinguishing HCC from cirrhosis and for distinguishing HCC from normals, indicating that CEA is a highly discriminatory marker for specific detection of HCC cases in patient populations that may potentially include patients with cirrhosis.

TABLE 5

Normalized median difference scores were calculated for each biomarker as $[(D - N))/\sqrt{(\sigma_D * \sigma_N)}]$ for HCC versus normal (HCC/N), HCC versus cirrhosis (HCC/C), or cirrhosis versus normal (C/N) samples. D = median concentration of biomarker for case sample set, N = median concentration of biomarker for control sample set (LOG transformed data). $\sigma_D$ and $\sigma_N$ = standard deviation of concentrations for case or control sets (LOG transformed data), respectively.

|  | AFP | CA 19.9 | CA 125 | CEA |
|---|---|---|---|---|
| HCC/N | 3.6 | 3.0 | 4.6 | 4.5 |
| HCC/C | 1.8 | 1.5 | 2.6 | 5.9 |
| C/N | 0.7 | 0.8 | 1.8 | 0.3 |

Example 3

Using Multi-Parameter Analysis for Distinguishing Normal, HCC and/or Cirrhotic Patients The levels of AFP, CA 125, CEA, and CA 19-9 in HCC samples were highly correlated to each other, as summarized in Table 6, which tabulates the correlation coefficients for the concentrations of these markers in the HCC samples.

TABLE 6

Correlation coefficients for the observed concentrations of AFP, CA 19-9, CA 125, and CEA in 25 HCC samples.

|  | AFP (ng/ml) | CA 19-9 (U/ml) | Ca125 (U/ml) | CEA (ng/ml) |
|---|---|---|---|---|
| AFP (ng/ml) | 1.0 |  |  |  |
| CA 19-9 (U/ml) | 0.9 | 1.0 |  |  |
| Ca125 (U/ml) | 1.0 | 0.9 | 1.0 |  |
| CEA (ng/ml) | 0.9 | 0.7 | 0.9 | 1.0 |

Figure 2A:
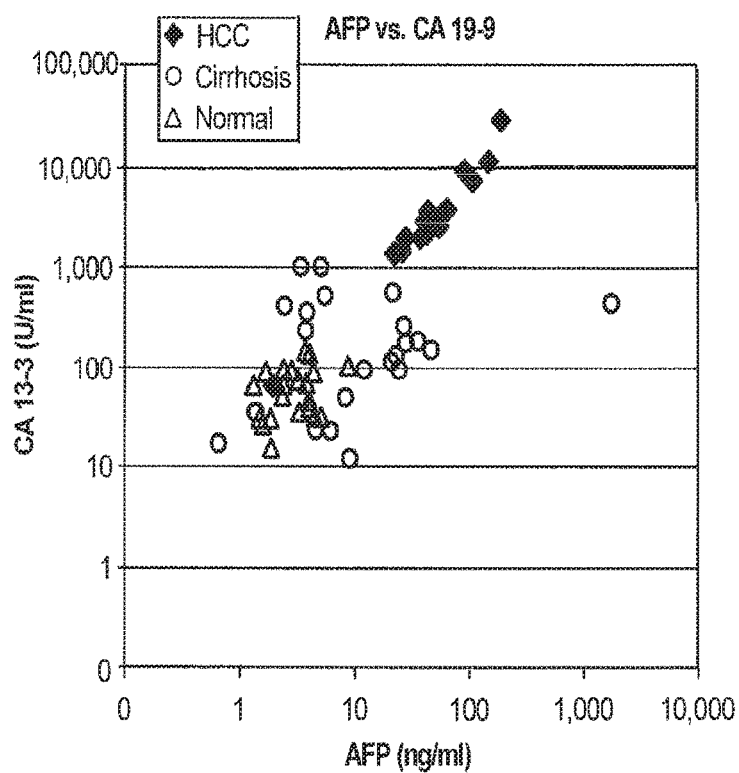
FIG. 2(A-L) shows a two dimensional analysis of biomarker pairs, in which the concentrations of selected biomarker pairs were plotted against each other to determine if a multi-parameter analysis improved the discrimination of HCC cases from controls. The concentrations of selected biomarker pairs were plotted against each other to determine whether the use of two biomarkers improved the ability to distinguish HCC cases from controls. The plots show results for the following biomarker pairs: AFP v. CA19-9 (Panel A), CA19-9 v. CA125 (Panel B), AFP v. CA125 (Panel C), CA19-9 v. MMP-9 (Panel D), AFP v. MMP-9 (Panel E), AFP v. OPN (Panel F), CA 125 v. OPN (Panel G), CA19-9 V. OPN (Panel H), CA125 v. MMP-9 (Panel I), AFP v. E-cadherin (Panel J), CA19-9 v, ErbB2 (Panel K), and CA19-9 v. E-Cadherin (Panel L).
Figure 2B:
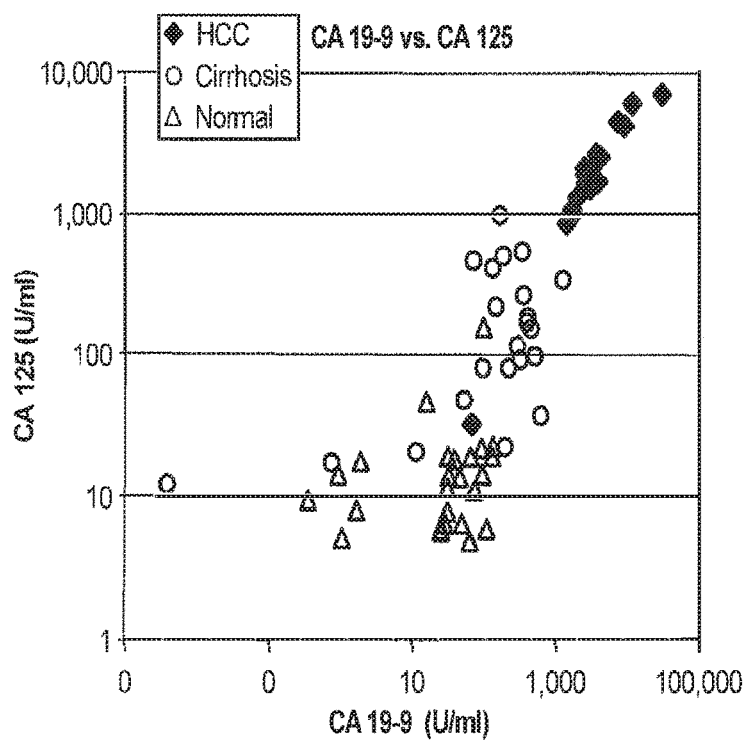
Figure 2C:
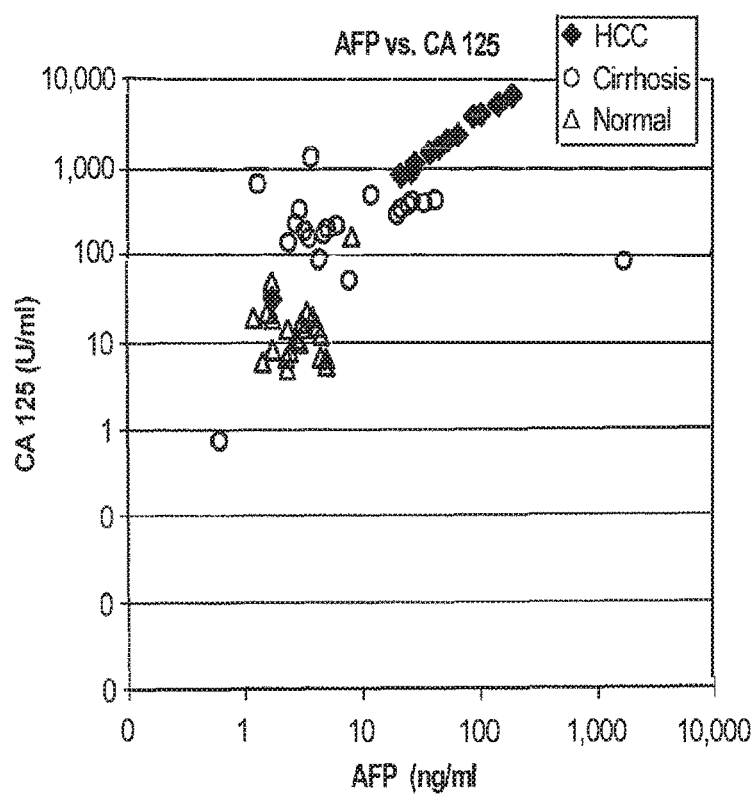
Figure 2D:
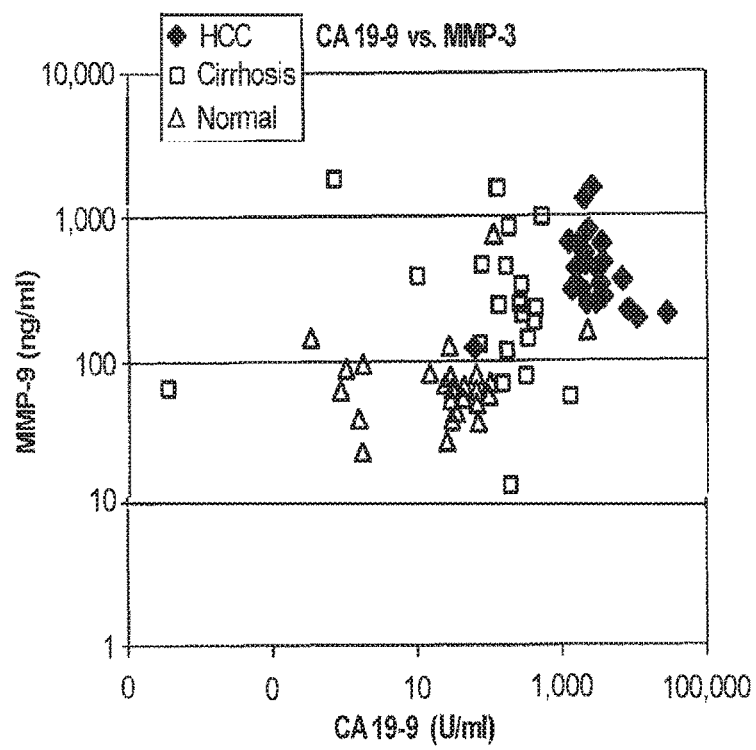
Figure 2E:
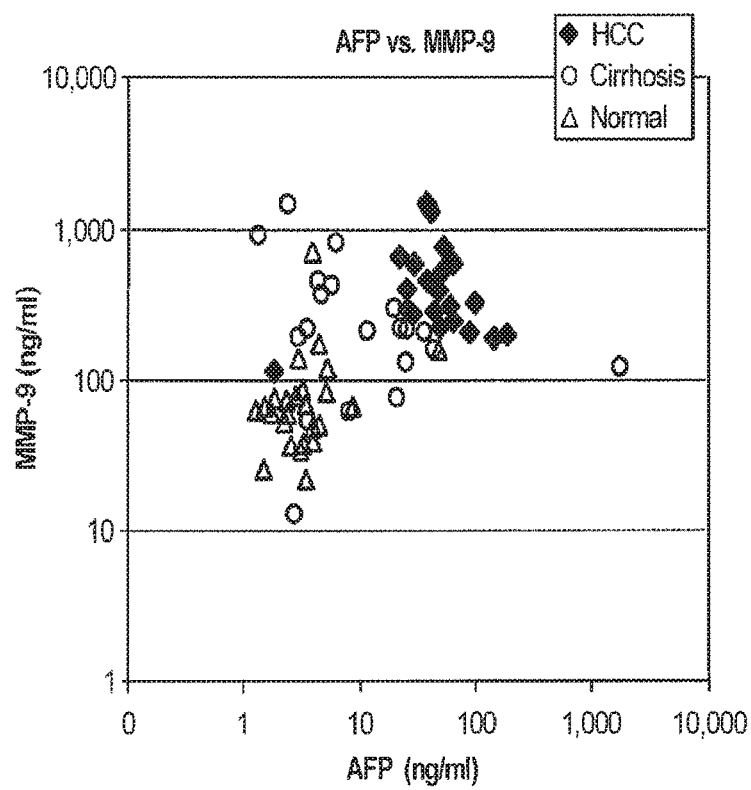
Figure 2F:
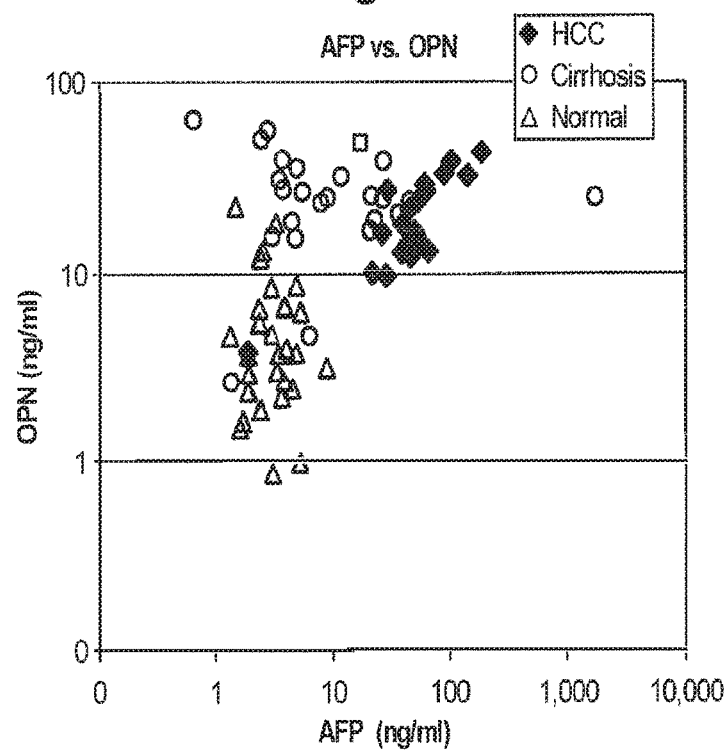
Figure 2G:
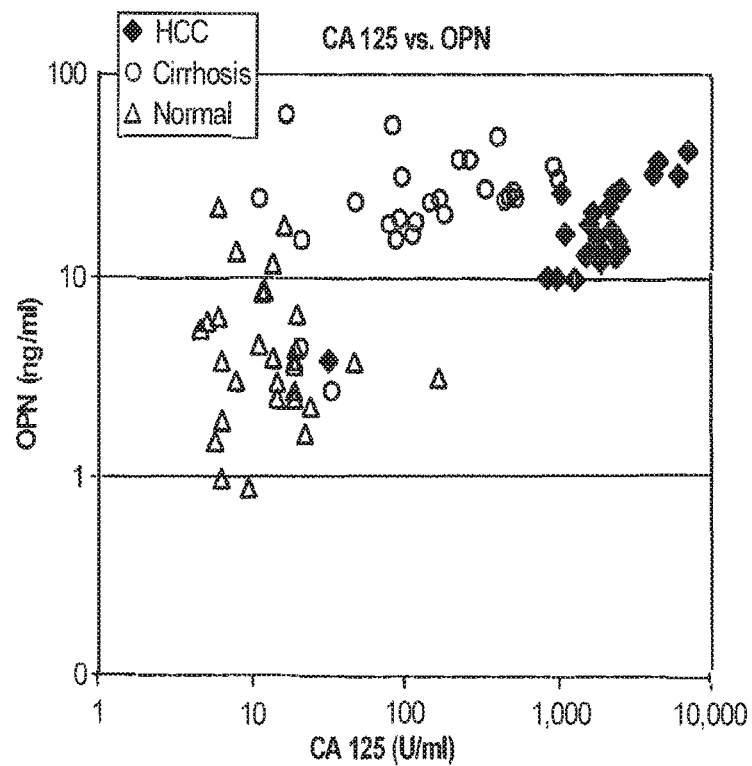
Figure 2H:
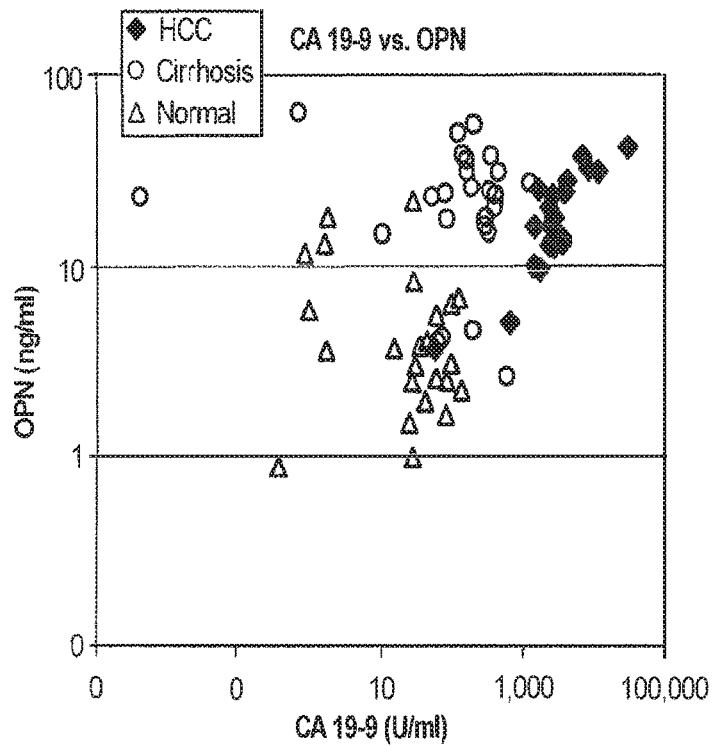
Figure 2I:
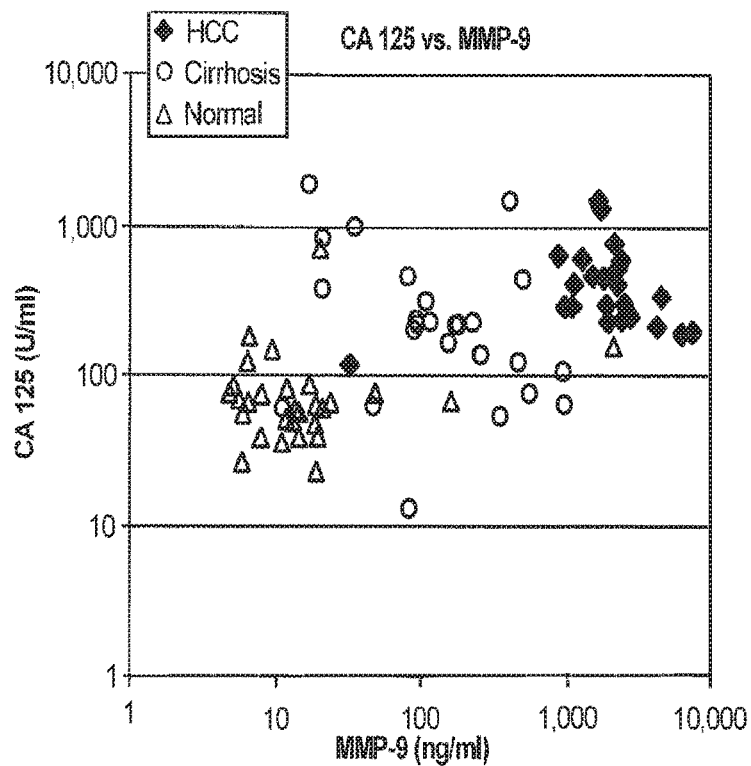
Figure 2J:
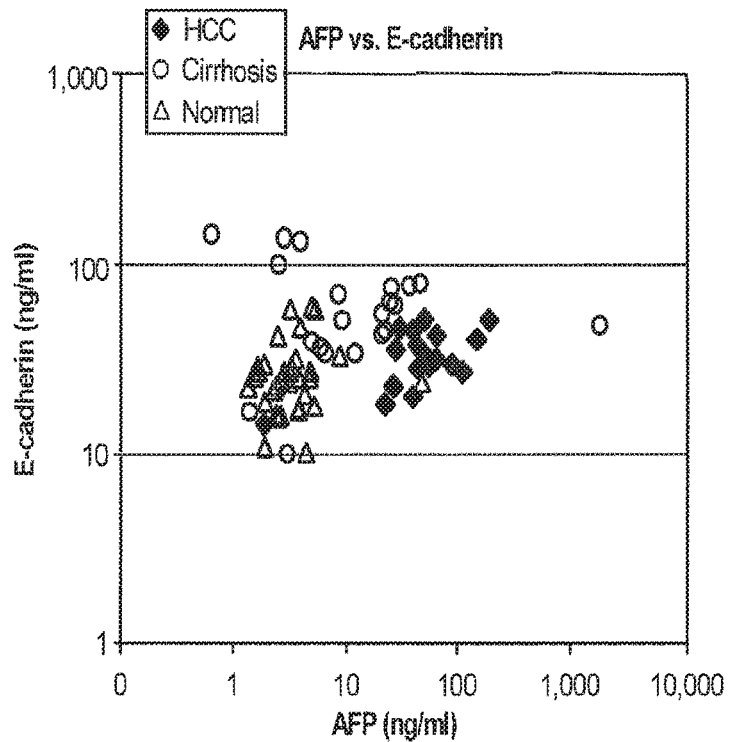
Figure 2K:
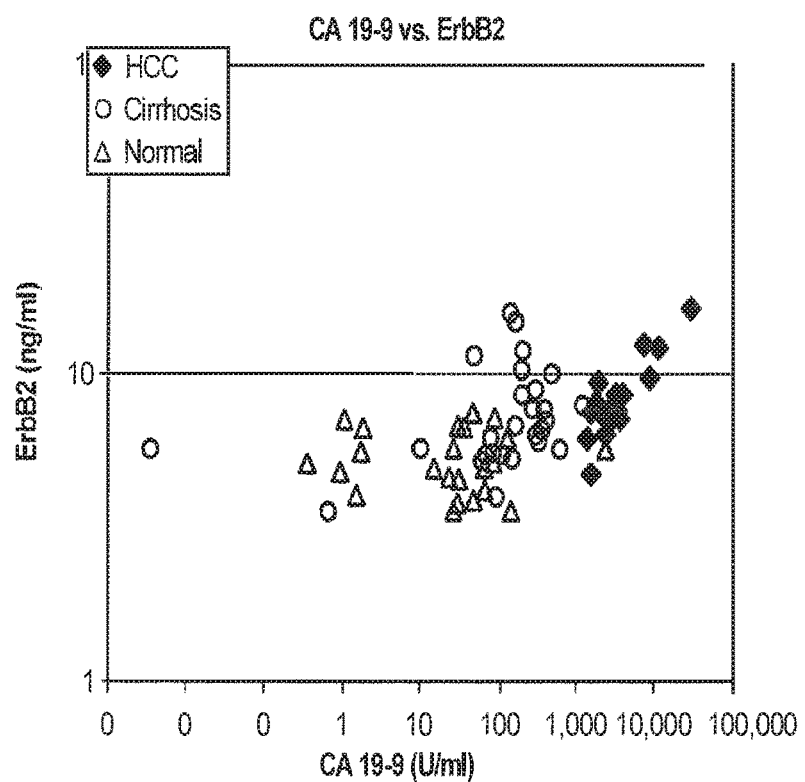
Figure 2L:
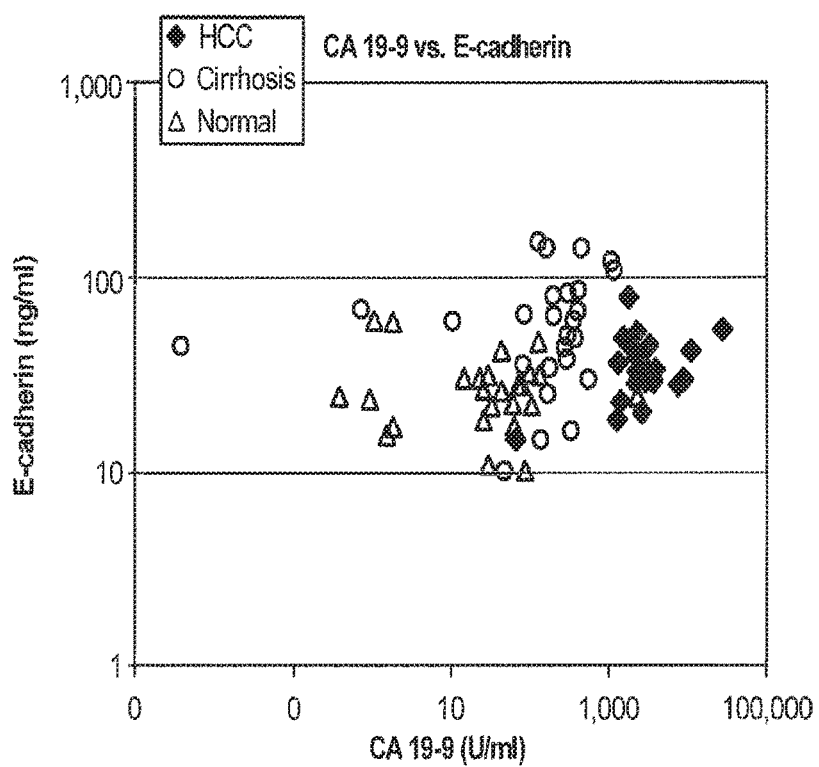

Analysis of pairs of markers showed an improved ability to distinguish HCC samples from cirrhosis and normal samples as shown visually in the 2-dimensional plots in FIG. 2 and through the calculated assay sensitivities and specificities presented in Tables 7 and 8. For the calculations of sensitivity and specificity, concentration cut-off values were selected for individual markers based on their ability to separate HCC cases from cirrhotic patients and normal controls. For each individual marker, Tables 7 and 8 provide the selected cut-off values, the sensitivity for HCC detection and the specificity for discriminating against normal patients (Table 7) and cirrhotic patients (Table 8). The tables also provide calculated sensitivity and specificity for pairs of markers determined by using the same cut-off values as for the individual assays, but requiring both markers to be positive for HCC to classify a sample as HCC. The tables demonstrate that, even using this simple algorithm, specificity was substantially increased by combining the listed biomarkers (especially for differentiating HCC and cirrhotic patients) with little or no cost to assay sensitivity. Combinations of these biomarkers should provide superior performance as compared to existing HCC detection modalities.

TABLE 7

Effect of combining results from pairs of biomarkers on the ability to detect HCC cases and differentiate HCC cases from normal controls. For assays using individual biomarkers, samples were classified as HCC positive if they met the cut-off criteria listed next to the individual biomarker names. For pairs of biomarkers, samples were classified as HCC positive if the result for both individual biomarkers was HCC positive. Sensitivity is defined as the percent of HCC samples correctly classified as HCC. Specificity is defined as percent of non-HCC (normal) samples correctly classified as non-HCC.

|  | Sensitivity | Specificity |
|---|---|---|
| Performance Using Individual Biomarkers | | |
| AFP (>21 ng/ml) | 96% | 97% |
| CA125 (>800 U/ml) | 96% | 97% |
| CA19-9 (>1350 U/ml) | 96% | 97% |
| MMP9 (>190 ng/ml) | 96% | 97% |
| E-cadherin (<48 ng/ml) | 88% | 7% |
| Performance Using Pairs of Biomarkers | | |
| AFP + CA125 | 96% | 97% |
| MMP9 + CA125 | 96% | 100% |
| CA19-9 + MMP9 | 96% | 100% |
| CA125 + E-cadherin | 92% | 97% |
| AFP + E-cadherin | 84% | 97% |
| AFP + MMP9 | 96% | 100% |

TABLE 8

Effect of combining results from pairs of biomarkers on the ability to detect HCC cases and differentiate HCC cases from cirrhosis cases. For assays using individual biomarkers, samples were classified as HCC positive if they met the cut-off criteria listed next to the individual biomarker names. For pairs of biomarkers, samples were classified as HCC positive if the result for both individual biomarkers was HCC positive. Sensitivity is defined as the percent of HCC samples correctly classified as HCC. Specificity is defined as percent of non-HCC (cirrhotic) samples correctly classified as non-HCC.

|  | Sensitivity | Specificity |
|---|---|---|
| Performance Using Individual Biomarkers | | |
| AFP (>21 ng/ml) | 96% | 72% |
| CA125 (>800 U/ml) | 96% | 92% |
| CA19-9 (>1350 U/ml) | 96% | 100% |
| MMP9 (>190 ng/ml) | 96% | 40% |
| E-cadherin (<48 ng/ml) | 88% | 60% |
| Performance Using Pairs of Biomarkers | | |
| AFP + CA125 | 96% | 100% |
| MMP9 + CA125 | 96% | 100% |
| CA125 + E-cadherin | 92% | 96% |
| AFP + E-cadherin | 84% | 96% |
| AFP + MMP9 | 96% | 84% |
| AFP + CA125 | 96% | 100% |

Various publications and test methods are cited herein, the disclosures of which are incorporated herein by reference in their entireties, In cases where the present specification and a document incorporated by reference and/or referred to herein include conflicting disclosure, and/or inconsistent use of terminology, and/or the incorporated/referenced documents use or define terms differently than they are used or defined in the present specification, the present specification shall control.

The invention claimed is:

1. A method for detecting hepatocellular carcinoma (HCC) in a patient, said method comprising:
   (a) obtaining a test sample from the patient;
   (b) measuring levels of a set of biomarkers in a test sample obtained from a patient, wherein said set of biomarkers comprises one of (1) AFP and CA125, (2) AFP and E-cadherin, and (3) AFP and MMP9;
   (c) comparing said levels of said set of biomarkers in said test sample to a detection cut-off level for each individual biomarker in the said set of biomarkers, wherein the detection cut-off level for AFP is >21 ng/mL, the detection cut-off level for CA 125 is >800 U/mL, the detection cut-off level for E-cadherin is <48 ng/mL, the detection cut-off level for MMP9 is >190 ng/mL;
   (d) detecting the presence or absence of HCC in said patient, wherein a detection is positive for HCC if the levels of at least two biomarkers in the measured set meet or exceed the detection cut-off level for the at least two biomarkers, wherein said levels of said set of biomarkers in said test sample are measured using an immunoassay; and
   (e) administering a therapeutic agent to said patient if the detection is positive for HCC.

2. The method according to claim 1, further comprising determining from said comparing step the disease progression of HCC.

3. The method according to claim 1, wherein said patient has been diagnosed with liver disease.

4. The method according to claim 3, wherein said liver disease is selected from the group consisting of cirrhosis, fibrosis, hepatitis, alcoholic liver disease, fatty liver disease, and combinations thereof.

5. The method according to claim 1, wherein said method further comprises subjecting said patient to an imaging method to evaluate the size, shape and position of the liver and said detecting step further comprises evaluating the presence or absence of HCC in said patient based on the results from said imaging method and said comparing step.

6. The method of claim 1, wherein said method differentiates HCC from non-cancerous liver diseases.

7. The method according to claim 1, wherein levels of said set of biomarkers are measured in a multiplexed assay.

8. The method according to claim 1, wherein levels of said set of biomarkers are measured in a single assay chamber.

9. The method according to claim 1, wherein said sample is selected from the group consisting of blood, serum and plasma.

10. The method according to claim 1, further comprising determining from said levels of said set of biomarkers the disease progression of HCC.

11. The method according to claim 1, wherein the set of biomarkers is AFP and CA125.

12. The method according to claim 1, wherein the set of biomarkers is AFP and E-cadherin.

13. The method according to claim 1, wherein the set of biomarkers is AFP and MMP9.

* * * * *